United States Patent
Senegas

(10) Patent No.: US 10,932,824 B2
(45) Date of Patent: *Mar. 2, 2021

(54) DYNAMICALLY STABILIZING INTERVERTEBRAL IMPLANT AND TOOL FOR POSITIONING SAME

(71) Applicant: BACKBONE, Le Bouscat (FR)

(72) Inventor: Jacques Senegas, Mérignac (FR)

(73) Assignee: BACKBONE, Le Bouscat (FR)

( * ) Notice: Subject to any disclaimer, the term of this patent is extended or adjusted under 35 U.S.C. 154(b) by 198 days.

This patent is subject to a terminal disclaimer.

(21) Appl. No.: 15/999,441

(22) PCT Filed: Feb. 15, 2017

(86) PCT No.: PCT/FR2017/050345
§ 371 (c)(1),
(2) Date: Nov. 21, 2018

(87) PCT Pub. No.: WO2017/140983
PCT Pub. Date: Aug. 24, 2017

(65) Prior Publication Data
US 2020/0107864 A1    Apr. 9, 2020

(30) Foreign Application Priority Data
Feb. 15, 2016  (FR) .................... 16 51206

(51) Int. Cl.
*A61B 17/70* (2006.01)
*A61B 17/88* (2006.01)

(52) U.S. Cl.
CPC ...... *A61B 17/7062* (2013.01); *A61B 17/7053* (2013.01); *A61B 17/7083* (2013.01); *A61B 17/8869* (2013.01)

(58) Field of Classification Search
CPC ............ A61B 17/7062; A61B 17/7053; A61B 17/7083; A61B 17/8869
(Continued)

(56) References Cited

U.S. PATENT DOCUMENTS

| | | | | |
|---|---|---|---|---|
| 5,496,318 A | * | 3/1996 | Howland | A61B 17/7053 606/249 |
| 6,761,720 B1 | * | 7/2004 | Senegas | A61B 17/7053 606/249 |

(Continued)

FOREIGN PATENT DOCUMENTS

| | | |
|---|---|---|
| EP | 2 138 122 A1 | 12/2009 |
| EP | 2 184 023 A1 | 5/2010 |

(Continued)

OTHER PUBLICATIONS

International Search Report, dated May 12, 2017, from corresponding PCT/FR2017/050345 application.

Primary Examiner — Eduardo C Robert
Assistant Examiner — David C Comstock
(74) Attorney, Agent, or Firm — Nixon & Vanderhye

(57) ABSTRACT

Disclosed is a dynamically stabilizing intervertebral implant including a stabilizing wedge, a flexible link in the form of a strap, and a blocking pin. The body of the stabilizing wedge includes a recess extending along a longitudinal axis, coincident with the posterior approach axis, and through which the strap passes. The blocking pin can engage inside the recess by movement in the recess longitudinal direction. The strap is immobilized with respect to the stabilizing wedge by being clamped between the pin and the facing recess wall. An tubular implant holder has an internal channel through which the blocking pin can be inserted and guided as far as the recess, in the direction of the longitudinal axis of the recess, when the implant holder is fixed to (Continued)

the stabilizing wedge so the internal channel and the recess are in parallax relative to each other.

18 Claims, 5 Drawing Sheets

(58) Field of Classification Search
USPC .................................................. 606/248, 249
See application file for complete search history.

(56) References Cited

U.S. PATENT DOCUMENTS

| | | | |
|---|---|---|---|
| 6,946,000 B2* | 9/2005 | Senegas | A61B 17/7062 606/248 |
| 8,221,464 B2* | 7/2012 | Belliard | A61B 17/7062 606/248 |
| 8,663,283 B2* | 3/2014 | Belliard | A61B 17/7053 606/248 |
| 10,595,910 B2* | 3/2020 | Senegas | A61B 17/7053 |
| 2009/0292317 A1 | 11/2009 | Belliard | |

FOREIGN PATENT DOCUMENTS

| | | |
|---|---|---|
| EP | 2 192 863 A | 9/2011 |
| EP | 2 515 778 A1 | 10/2012 |
| WO | 2011/077101 A1 | 6/2011 |

* cited by examiner

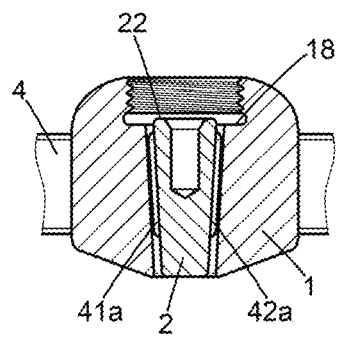 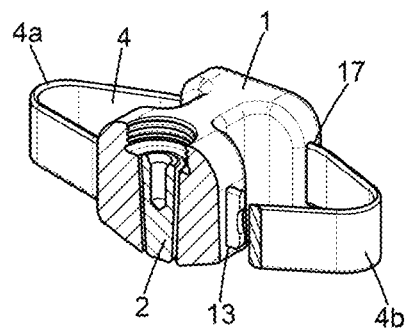
FIG. 5A  FIG. 5B
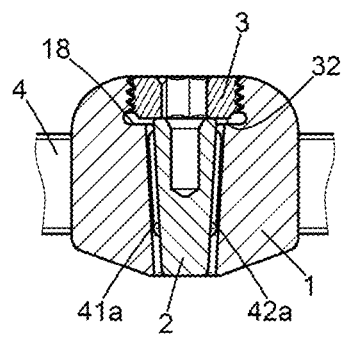 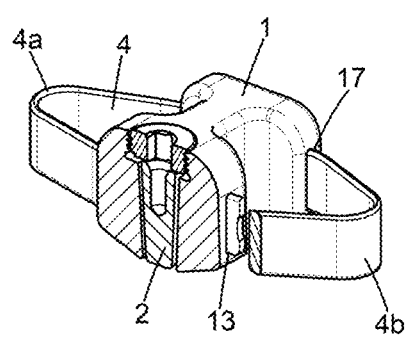
FIG. 6A  FIG. 6B
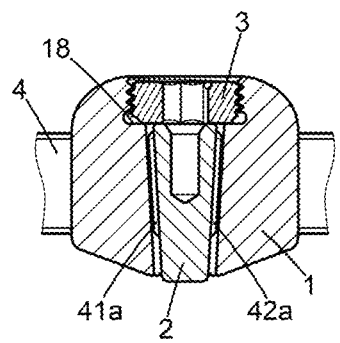 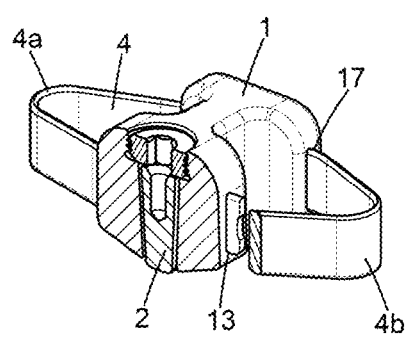
FIG. 7A  FIG. 7B

DYNAMICALLY STABILIZING INTERVERTEBRAL IMPLANT AND TOOL FOR POSITIONING SAME

TECHNICAL FIELD

The present invention relates generally to implants used in surgery of the spine, more particularly to a surgical kit comprising a dynamically stabilizing intervertebral implant and a tool for positioning same.

Technological Background

Operations performed in surgery of the spine may concern the cervical region (neck), the thoracic region or, more frequently, the lumbar region.

When there is an instability, for example sliding of one vertebra relative to the adjacent vertebrae, an operation for stabilizing the spinal column may entail implanting metal material in the form of screws connected to each other by bars or plates. These implants form scaffolding that acts as a stabilizer for the spinal column.

In more recent techniques, the stabilization of the column can be obtained by means of an intervertebral implant consisting of a stabilizing wedge, a flexible link in the form of a textile braid, a movable assembly and a locking member. The stabilizing wedge is intended to be positioned between the spinous processes of two consecutive vertebrae, that is to say adjacent vertebrae, that are to be stabilized. The flexible link (for example a textile braid) encloses the spinous processes. The movable assembly is adapted to come into engagement with the stabilizing wedge in such a way as to immobilize the flexible link with respect to the stabilizing wedge. This blocking is achieved by clamping the flexible link between the movable assembly and the stabilizing wedge. The locking member (for example a screw) is adapted to lock the engagement of the movable assembly with the stabilizing wedge, and thus the final blocking of the flexible link, which results directly from this.

PRIOR ART

An intervertebral implant of the aforementioned type is disclosed, for example, in the document EP 2515778, published by WIPO under number WO 2011/077101. More particularly, this document describes a device which has a wedge body with a first face and a second face, two clamps or locks positioned on each of the faces, and two bands forming flexible links. The wedge body has an internally threaded orifice, which is provided on a face of the wedge body directed to the rear and which is adapted to receive the attachment of an implant holder. According to the disclosed teaching, the implant holder is used for gripping the wedge during its positioning in the zone to be treated and for clamping the flexible links. Indeed, a clamping guide can be placed over the implant holder in order to receive a third tool for tensioning the flexible links.

Most of the lumbar operations are performed by open surgery using a posterior approach, by making an incision in the patient's back at the level of the vertebrae that are to be stabilized.

The design of the implants of the prior art involves the surgeon having to clear quite a wide intervention region around the vertebrae that are to be stabilized, in particular for placing the one or more flexible links in the wedge, and for tensioning and blocking said one or more links.

In recent years, research and development efforts have focused primarily on the means and mechanisms by which the assembly, formed by the stabilizing wedge on the one hand and by the one or more flexible links on the other hand, is kept in place. More particularly, the experience gained by surgeons shows that the following aspects need to be taken into account for tensioning and maintaining the tension of the one or more flexible links:

- embodiment of the clamping on the flexible link, which can be perpendicular, posterior, tangential, parallel to a longitudinal axis of the link;
- number of fixed or movable components that are needed; and
- degree of ease with which the surgeon performs the operation (assessed in particular on the basis of the number of steps and the number of instruments, the position in the surgical wound, etc.).

The document EP 2138122 describes a system for stabilization between the sacrum and a lumbar vertebra. The system comprises at least one textile braid which is anchored on the sacrum by screws. To ensure that the braids are blocked with tensioning, a blocking system comprises wedging pins between the inner walls of an orifice provided in the body of the blocking system. The direction of movement of such a movable pin is tangential to the surface of the braid and is parallel to the longitudinal axis of said braid. These arrangements are not adapted to an intervertebral implant of the kind forming the subject matter of the present invention.

SUMMARY OF THE INVENTION

It is important to provide the surgeon with a dynamically stabilizing intervertebral implant and with surgical instruments for its placement in a surgical environment, which makes it possible to reduce the size of the incision to an absolute minimum. Indeed, it is necessary to protect the surrounding tissue (in particular the muscle tissue that contributes to the stability of the spinal column) from the stress associated with the retraction of the surgical wound, which can cause severe necrosis. The patient's recovery after surgery is all the more rapid and the result all the more satisfactory.

To this end, the invention proposes a surgical kit comprising:

an intervertebral implant with:
- a stabilizing wedge adapted to stabilize at least two adjacent vertebrae by interposition between spinous processes of the vertebrae, having a substantially parallelepipedal body which has a defined main axis and in which is provided a recess having a defined longitudinal axis parallel to the main axis of the body of the stabilizing wedge; and
- at least one strap forming a flexible link for fixing the stabilizing wedge to the spinous processes of the vertebrae to be stabilized, said strap having first and second portions which each comprise one of the opposite ends of said strap; and also
- an implant holder having an elongate body along a defined longitudinal axis and with a first end and a second end, and having fixing means which are provided at the first end and which are adapted to cooperate with associated means provided at the body of the stabilizing wedge of the implant for fixing the implant holder to the body of the stabilizing wedge in such a way that the elongate body of said implant holder is in parallax with said recess.

According to embodiments of the kit according to the invention:

the recess provided in the body of the stabilizing wedge comprises an inner wall extending parallel to the longitudinal axis of the recess and has a defined shape;

at least the first strap portion can pass through the recess perpendicularly with respect to the longitudinal axis of said recess;

the intervertebral implant further comprises a blocking pin having a defined longitudinal axis and a defined shape substantially complementing the shape of the recess provided in the body of the stabilizing wedge, in order to come into engagement with said stabilizing wedge by movement in said recess in the direction of the longitudinal axis of said recess, so as to immobilize the strap with respect to the stabilizing wedge by clamping the strap portion between the blocking pin and the inner wall of the recess; and furthermore the elongate body of the implant holder is tubular with an internal channel extending along the longitudinal axis of the elongate body of the implant holder and having an internal diameter slightly larger than the largest diameter of the blocking pin of the implant, in order to allow said blocking pin to be inserted and guided through said internal channel, as far as the recess provided in the body of the stabilizing wedge, in the direction of the longitudinal axis of said recess, when the implant holder is fixed to the stabilizing wedge.

The abovementioned main axis coincides with the axis of the posterior approach for the surgical operation to put the implant in place. Since the recess provided in the stabilizing wedge is open posteriorly when the wedge is in the installation position, its longitudinal axis corresponds to the axis of the posterior approach (in contrast, for example, to a lateral access, these terms "posterior" or "lateral" being from the vocabulary used in this field of spinal surgery). The blocking pin can thus be conveniently and usefully inserted by force into the recess along the axis of the posterior approach. The region of intervention and insertion (open surgery) can thus be reduced to the absolute minimum. The invention thus permits a truly minimally invasive procedure and surgical treatment of the outpatient type.

Although a male frustoconical pin has already been used to block a textile braid in a blocking system as described in the document EP 2138122, its use as defined above in the context of a stabilizing wedge intended to be placed between the spinous processes of two consecutive vertebrae to stabilized is original. The invention is distinguished particularly in terms of the positioning of the movable element formed by the blocking pin, which is obtained by applying a force along the axis of the posterior approach only, by means of a single instrument for aligning, guiding and inserting the blocking pin. The invention is also original in the use of a blocking pin in combination with a flexible link of the strap type or flat braid, perpendicular to the longitudinal axis of the strap and in the strict posterior plane of the implant and of the surgical wound. These arrangements permit a truly minimally invasive procedure and a surgical treatment of the outpatient type.

According to other embodiments, the recess provided in the body of the stabilizing wedge can have an internally threaded inlet zone, and the tubular body of the implant holder can have, at its first end, a thread adapted to cooperate with the internal thread of the inlet zone of the recess in order to fix the implant holder to the stabilizing wedge by screwing. The internal channel of the implant holder is thus directly in parallax with the recess provided in the stabilizing wedge in order to receive the blocking pin.

According to other embodiments, considered individually or in combination:

the surgical kit can further comprise an insertion rod for the blocking pin, having a first end and a second end and being adapted to slide in the internal channel of the tubular body of the implant holder for inserting and guiding the blocking pin through the internal channel of the implant holder as far as the recess provided in the body of the stabilizing wedge; the engagement of the blocking pin in the recess is greatly facilitated in this way;

the surgical kit can further comprise a connecting piece for fixing the blocking pin detachably to the second end of the insertion rod; this avoids any risk of the pin dropping into the wound during the operation; this connection also makes it possible to manipulate the pin (for example in rotation about its longitudinal axis) directly via the insertion rod;

the blocking pin can have, at the rear, a recess extending in the longitudinal direction of said pin; the second end of the insertion rod can then comprise an internally threaded recess extending in the longitudinal direction of said rod; and the connecting piece can be a ferrule having, on the one hand, a first threaded end part adapted to cooperate with the internal thread of the recess provided at the second end of the insertion rod, and, on the other hand, a second, conical end part adapted to be engaged by force into the recess provided at the rear of the blocking pin in order to achieve the detachable fixing of said blocking pin to said insertion rod. The connecting piece can then be of a disposable type, while being firmly attached to the end of the insertion rod.

In another embodiment, the implant holder can be provided with an internal thread at its second end, at a free inlet of the internal channel when the implant holder is fixed to the stabilizing wedge, and the insertion rod can be provided, at its first end, with a thread in order to cooperate with said internal thread in such a way that the insertion and then the screwing of the insertion rod into the internal channel of the implant holder drives the conical pin inside the recess provided in the body of the stabilizing wedge in the direction of the longitudinal axis of said recess. This permits good control of the advance of the pin inside the recess provided in the stabilizing wedge.

Moreover, the strap has a defined longitudinal direction and a defined strap surface, and the blocking pin can come into engagement with the stabilizing wedge by movement inside the recess provided in the body of the stabilizing wedge, in such a way that the longitudinal axis of the blocking pin:

firstly coincides with the longitudinal axis of the recess;

secondly is perpendicular to the longitudinal axis of the strap plogemortion inside the recess; and thirdly is parallel to the surface of the first strap portion inside the recess.

Alternatively, each of the first and second strap portions can pass through the recess provided in the stabilizing wedge, in order for the strap to form at least one loop in a plane perpendicular to the main axis of the wedge, with at least one cord adapted to come into engagement with one of the spinous processes of two vertebrae to be stabilized; and the blocking pin can come into engagement with the stabilizing wedge in the direction of the main axis of the body of said wedge, between each of the first and second strap portions inside the recess, in such a way that the longitudinal axis of the pin:

firstly coincides with the longitudinal axis of the recess;
secondly is perpendicular to the longitudinal axis of each of the two portions of the strap inside the recess; and
thirdly is parallel to the surface of each of the first and second strap portions inside the recess, moreover in such a way that each of the first and second strap portions is immobilized with respect to the stabilizing wedge by said strap portion being clamped between the blocking pin and respective portions of the inner wall of the recess that face each other.

The first and second strap portions can then pass in opposite directions through the recess provided in the body of the stabilizing wedge, so as to intersect in said recess, and in order for the strap to form a loop in a plane perpendicular to the main axis of the wedge, with two cords which are located respectively on either side of the stabilizing wedge in said plane and are adapted to come into engagement each with a respective one of the spinous processes of two adjacent vertebrae to be stabilized.

Finally, the surgical kit can further comprise a screw of the same diameter as the diameter of the inlet zone of the recess provided in the body of the distributing wedge, with a thread adapted to cooperate with the internal thread of said inlet zone, and with a bearing zone adapted to bear against a contact zone at the rear of the blocking pin in order to axially lock the engagement of the blocking pin in the recess provided in the stabilizing wedge and thus the blocking of the strap.

BRIEF DESCRIPTION OF THE DRAWINGS

Other features and advantages of the invention will become clear on reading the following description. The latter is given purely as an illustration and must be read with reference to the attached drawings, in which:

FIG. 5A and FIG. 5B are a sectional view and a three-dimensional sectional view, respectively, of the stabilizing wedge provided with the strap and the installed blocking pin, according to embodiments;

FIG. 6A and FIG. 6B are views identical to those of FIGS. 5A and 5B, respectively, additionally showing the locking screw engaged at the inlet of the recess in the wedge;

FIG. 7A and FIG. 7B are views identical to those of FIGS. 5A and 5B, respectively, additionally showing the locking screw in the locking position;

DETAILED DESCRIPTION OF EMBODIMENTS

The intervertebral implant is designed to be placed between the spinous processes of two adjacent vertebrae, that is to say consecutive vertebrae in the stack of lumbar, thoracic and cervical vertebrae.

The main elements of the dynamically stabilizing intervertebral implant according to embodiments of the present invention will be described first with reference to FIGS. 1 and 2. As is shown in these figures, the implant is composed of a stabilizing wedge 1, a blocking pin 2, a locking screw 3, and a flexible link 4.

Figure 1:
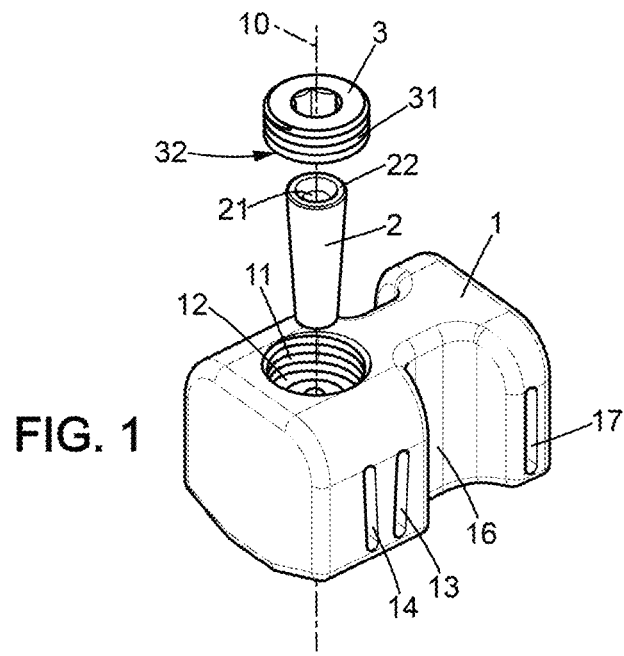
FIG. 1 is an exploded three-dimensional view of a part of the intervertebral implant according to embodiments.

The stabilizing wedge 1 comprises a generally parallelepipedal body with a main axis which, for the sake of clarity in FIG. 1, is coincident in this figure with the longitudinal axis 10 of a recess 12 which is provided in the body and which will be discussed later. FIG. 2 is a view of the implant along the longitudinal axis 10, when the implant is placed flat against the vertebrae of the patient (who is lying face down on the operating table). The main axis 10 then coincides with the axis of the posterior approach, that is to say it is perpendicular to the patient's back and therefore to the axis of the vertebral column corresponding to the direction of stacking of the vertebrae from the lumbar vertebrae to the cervical vertebrae.

As regards the descriptive terminology, the direction in which the surgeon views the implantation site is considered hereinbelow to be along the axis of the posterior approach, during the implantation procedure and when the patient is lying face down on the operating table. FIG. 2 thus shows a front view along this axis, and a plan view along this direction. The terms "posteriorly", "front" and "rear", "in front of" and "behind", "front" and "rear", "above" and "below", "upper" and "lower", "up" and "down", "lateral" and "side", "right" and "left", especially, are used hereinbelow with reference to this convention. These terms thus correspond to the vocabulary used by persons skilled in the art of surgery of the spine.

Figure 2:
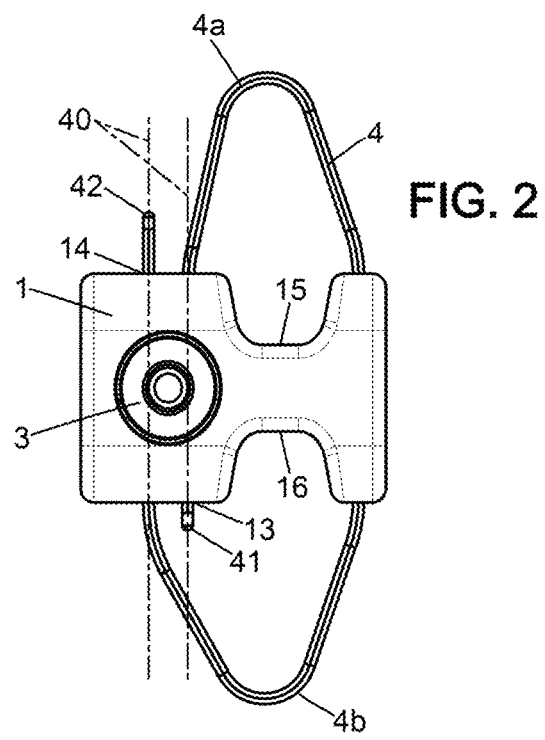
FIG. 2 is a front view, along the axis of the posterior approach, of the assembled implant according to embodiments.

The body of the stabilizing wedge 1 comprises, on a lateral face of the parallelepiped, in particular to the right in FIGS. 1 and 2, an upper indentation or notch 15 and a lower indentation or notch 16. These indentations are adapted to bear against two vertebrae to be stabilized, more particularly on the spinous process of the upper vertebra via the notch 15 and on the spinous process of the lower vertebra via the notch 16, respectively. In other words, in the installed position of the implant for stabilization of two adjacent vertebrae, the spinous processes of these vertebrae are housed in the indentations 15 and 16 of the body of the wedge 1.

As can be seen in FIG. 1, the parallelepiped of the body of the wedge 1 has softened (i.e. rounded) angles, at least on the rear face intended to be covered by flesh and skin of the patient's back. This limits the risk of inflammation or damage to the dorsal flesh in contact with the implant. This likewise reduces the discomfort or indeed the pain that the patient may feel if pressure is applied to this region of his back, for example when resting against a support (for example a seat back) or lying on his back (for example on a hard surface such as the ground).

The blocking pin 2 can have a cylindrical and conical shape, that is to say have the shape of a cylinder whose cross-sectional diameter (circular) gradually decreases along its longitudinal axis. In FIG. 1, again for the sake of clarity of the drawing, the longitudinal axis of the pin coincides with the main axis 10 of the body 1 of the wedge and with the longitudinal axis of the recess 12.

The pin 2 is adapted to cooperate with the recess 12 provided in the body of the wedge 1, for example on the lateral face of the parallelepiped opposite to the face where the indentations 15 and 16 are located (i.e. to the left in FIGS. 1 and 2). For this purpose, the pin 2 and the recess 12 have shapes that complement each other. In the example shown, the pin has the shape of a conical cylinder, and the recess likewise has the shape of hollow conical cylinder with an aperture angle equal to that of the pin and an aperture diameter slightly greater than said diameter of the pin.

The recess opens out at least on the rear face of the wedge 1, and preferably on each of the front and rear faces of the wedge, as is shown in FIGS. 5A-5B, 6A-6B and 7A-7B. The diameter of the opening is substantially larger than the largest diameter of the pin and is constant in an inlet zone of the recess on the rear face via which the pin 2 is intended to enter with its tapered end. In this inlet zone of the recess, its walls have an internal thread 11 for the locking screw, which will be discussed later. The length of the inlet zone, along the longitudinal axis, is at least equal to the thickness of the locking screw 3. In front of this inlet zone, the shape of the recess is conical, without an internal thread (smooth walls), and substantially corresponds to the complementary shape of the pin, that is to say the shape is conical with the same aperture angle as that of the pin but with a slightly larger diameter in order to receive the pin and the braid, as will be explained later. In other words, in front of the threaded inlet zone of the recess, the diameter of the recess progressively decreases along its longitudinal axis 10 toward the front. In particular, the length of the conical part of the recess along the longitudinal axis of the recess is substantially equal to the length of the blocking pin 2 in its longitudinal direction.

The locking screw 3 is also shown in FIG. 1 in parallax with the main axis 10 of the body 1 of the wedge and the longitudinal axis of the recess 12. The screw 3 has a diameter larger than the largest diameter of the pin. This diameter corresponds to that of the internally threaded inlet zone of the recess 12. The screw 3 has an external thread 31, adapted to cooperate with the internal thread 11 of the recess 12.

The screw 3 additionally has a bearing zone 32, facing downward in FIG. 1, capable of abutting against a contact zone 22 at the rear of the pin 2. In one embodiment, the bearing zone 32 of the screw 3 and/or the contact zone 22 of the pin 2 are circular planar surfaces.

The function of the screw 3 is to lock the position of the pin 2 engaged in the recess 12. Another function of the screw, according to some embodiments, is to adjust the axial position of the pin in the recess: by turning the screw 3 engaged in the recess 12 via their respective threads, the screw rests with its surface 32 against a contact surface 22 on the rear of the pin 2, such that the latter advances through the recess 12 along its longitudinal axis, from the rear face of the wedge to the front face thereof. Details of this positional adjustment will be given later with reference to FIGS. 5A-5B, 6A-6B and 7A-7B.

Figure 3:
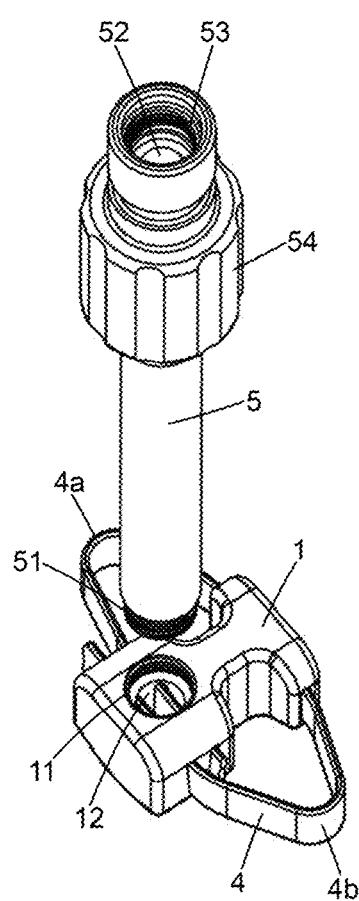
FIG. 3 is an exploded three-dimensional view of a part of the intervertebral implant and of an associated implant holder, according to embodiments.
Figure 10:
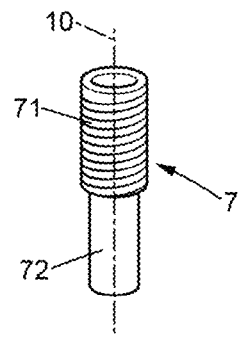
FIG. 10 is a three-dimensional view of a connecting piece providing a detachable connection between the blocking pin and the end of the insertion rod from FIG. 4.

The flexible link 4 can be a braid made of a textile material for medical use (non-resorbable), for example polyethylene terephthalate (PET) or polyethylene (PE). These materials can be chosen by reason of their biocompatibility and their high degree of chemical inertness. In the installed position of the implant, the flexible link 4 encloses the spinous processes in a similar way to that described in EP 2192863, particularly as shown in FIGS. 3, 10 and 11A of said published document.

The flexible link 4 preferably has the form of a strap (i.e. a tape), with a longitudinal axis and a strap surface extending along said longitudinal direction. It can pass through a passage 17 of the body of the wedge, provided in the caudal end of the body of the wedge on the right-hand side thereof, that is to say the side of the indentations 15 and 16 that is opposite to the recess 12. The passage 17 extends through the body of the wedge 1 perpendicularly with respect to the main axis 10 of the body 1 of the wedge. When not immobilized with respect to the wedge, the flexible link 4 can slide in the passage 17.

The flexible link 4 can also pass through the recess 12. For this purpose, the body of the wedge can have two other passages 13 and 14 extending right through the body 1 perpendicularly with respect to the main axis 10 of the body 1 of the wedge. At least one of the passages 13 and 14, preferably both passages 13 and 14, pass(es) through the recess 12. In other words, the passages 13 and 14 open into the recess. In the embodiment shown, the two passages 13 and 14 thus extend through the recess 12, but this is not obligatory, and it would be possible for just one of the passages 13 and 14 to extend through the recess 12. When it is not immobilized with respect to the wedge 1, the flexible link 4 can slide in the passages 13 and 14.

The flexible link 4 is inserted manually by the surgeon, for example first through the passage 17. Then the two ends 41 and 42 of the flexible link 4 are in turn inserted into the passages 13 and 14 after having engaged them above and below the spinous processes of the upper and lower vertebrae, respectively.

More particularly, the strap 4 then forms a loop in a plane perpendicular to the main axis 10 of the wedge 1, with at least one and preferably two cords 4a and 4b respectively located on either side of the wedge in said plane. These cords 4a and 4b of the textile braid are each adapted to come into engagement respectively with one of the spinous processes of the two vertebrae to be stabilized.

The blocking pin 2 can be engaged with the stabilizing wedge in the direction of the main axis 10 of the body 1 of the wedge between each of the strap portions inside the recess, such that the longitudinal axis of the pin:

firstly coincides with the longitudinal axis 10 of the recess;

secondly is perpendicular to the longitudinal axis 40 of each of the two portions of the strap inside the recess; and, thirdly is parallel to the surface of each of the two strap portions inside the recess (i.e. the strap portions at the ends 41 and 42, respectively, of the strap).

In addition, each of the portions of the strap, at its ends 41 and 42 respectively, is then immobilized with respect to the wedge 1. This blocking is obtained by clamping said strap portions between the pin and respective portions of the inner wall of the recess 12 that face each other.

To illustrate this blocking of the two portions of the strap 4 by the pin 2, the central part of FIGS. 5A, 6A and 7A, corresponding to the internal space of the recess (which receives the pin 2), is shown along a section plane at 90 degrees to the section plane of the body 1 of the wedge in the same figures. Thus, FIGS. 5A, 6A and 7A show, at their center, a sectional view of the portions 41a and 42a of the strap 40 at the ends 41 and 42, respectively, of said strap.

In one embodiment, these two end portions 41a and 42a of the strap can pass in opposite directions through the recess 12 provided in the wedge 1, so as to intersect in said recess and form the cords 4a and 4b. This embodiment is shown in the figures. However, it is not exclusive. Indeed, the two end portions 41a and 41b of the strap could extend parallel to each other through the passages 13 and 14, and therefore through the recess 12, given another form of engagement with the spinous processes of the vertebrae to be stabilized, and also given another shape of the stabilizing wedge. In particular, in such an embodiment, the strap would form only one cord, so that two straps would be used, namely one for each of the vertebrae, with the same wedge.

To facilitate the procedure of insertion through the passages 13 and 14, the ends 41 and 42 of the strap can be reinforced, for example by treatment with ultrasonic welding, by addition of material, or by an endpiece made of titanium, or of any other suitable material, or by any other equivalent means.

Advantageously, the means for locking and blocking the flexible link 4, which comprise the pin 2 and the screw 3, are put in place via the rear face of the stabilizing wedge 1. This arrangement allows the surgeon to reduce the size of the incision to an absolute minimum, thereby preserving the integrity of the surrounding organic tissue, especially the muscles of the back.

After the flexible link 4 has been put in place and tensioned with the aid of a suitable tool (procedure not described in the context of the present description), the blocking pin 2 is inserted into the recess 12, between the two end portions of the flexible link 4. The insertion of the pin 2 causes the clamping of the portions of the flexible link 4, between the outer circumferential surface of the pin 2 and the opposite inner wall of the recess 12, and stabilizes the flexible link 4. By virtue of this compression of the flexible link 4, the latter can no longer slide in the passages 13, 14 and 17. The locking screw 3 is then engaged in the recess 12, for example by hand (with or without the aid of a tool holder), once the conical pin 2 has been inserted fully into the internally threaded portion 11 of the recess 12, as shown in FIGS. 5A and 5B. This procedure is illustrated in FIGS. 6A and 6B. The function of the screw 3 is to secure (axially) the engagement of the blocking pin 2 in the recess 12.

Figure 4:
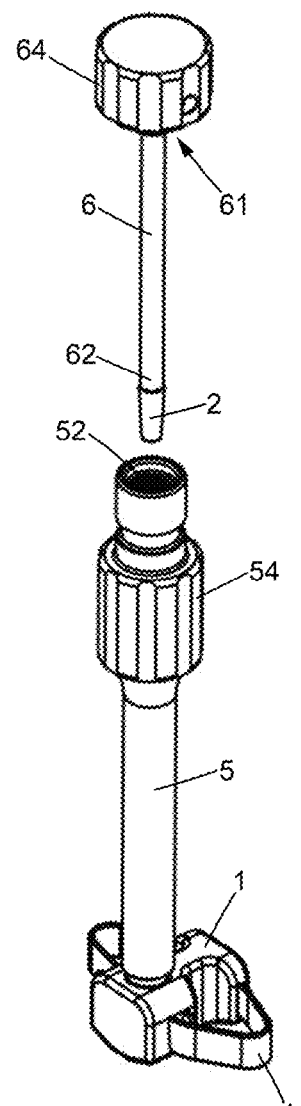
FIG. 4 is an exploded three-dimensional view of a part of the intervertebral implant with the implant holder holder mounted on the implant, and of an insertion rod for the blocking pin according to embodiments.

The method by which the conical blocking pin 2 is put in place makes use of an implant holder 5 and an insertion rod 6, which are shown in FIGS. 3 and 4. The implant holder 5 is, for example, a hollow tube, that is to say it has a tubular body having an internal channel 52. The channel 52 is, for example, of constant circular cross section, with an internal diameter slightly larger than the largest diameter of the blocking pin 2.

At one of the ends of the tube 5, an internal thread 53 can be provided at the entry to the channel 52. Likewise, gripping means, which may be in the form of a fluted collar 54 surrounding the tube 5 as shown, can be provided at this inlet end of the tube 5.

Figure 13:
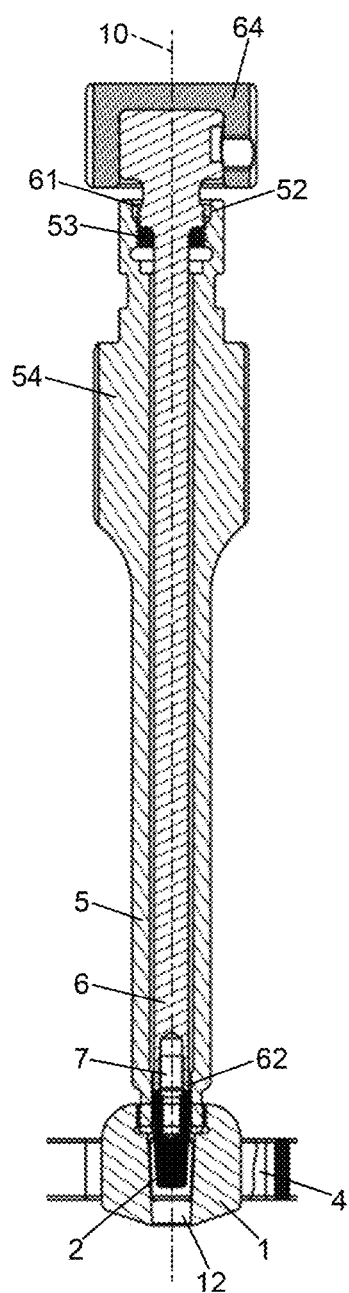
FIG. 13 is a sectional view of an implant holder fixed to the stabilizing wedge, with the insertion rod engaged in the channel of the implant holder, and the blocking pin fixed to the end of the connection rod and partially engaged in the recess provided in the body of the stabilizing wedge.

At the other of its ends, the tube 5 can be provided with an external thread 51 which cooperates with the internal thread 11 of the stabilizing wedge 1. The implant holder 5 can thus be screwed into the stabilizing wedge 1, with the internal channel 52 aligned with the longitudinal axis 10 of the recess 2, that is to say in parallax with the recess 12, for the purpose of inserting the blocking pin 2 into said recess 12 through the internal channel 52. This embodiment of the means for fixing the implant holder 5 to the body 1 of the wedge is also illustrated in FIG. 13, the description of which will be given later.

The fluted collar 54 by which the surgeon grips the implant holder is preferably close to the end of the tube 5 corresponding to the inlet of the internal channel 52, that is to say the end opposite the one which carries the thread 51 by which the implant holder is fixed to the wedge 1.

For the procedure of insertion into the recess 12, the blocking pin 2 can be fixed in an easily detachable manner to one end of the insertion rod 6. This detachable fixing can be achieved, for example, by means of an elastic connecting piece, the detailed description of which will also be given later.

The other end of the insertion rod 6 is provided with an external thread 61 below gripping means such as a fluted head 63, as shown. This thread (not visible in FIG. 4) cooperates with the internal thread 53 of the implant holder 5.

The insertion rod 6 and the conical pin 2 held detachably at the end thereof are introduced into the channel 52 of the implant holder 5, via the end thereof carrying the internal thread 53. The screwing of the insertion rod 6 into the channel 52 of the implant holder 5 drives the conical pin 2 into the recess 12 of the wedge 1. This screwing is obtained through the cooperation of the thread 61 of the rod 6 and the internal thread 53 of the implant holder 5. Thus, the engagement of the pin 2 by force in the conical and unthreaded portion of the recess 12, as has been indicated above, is obtained by this screwing of the insertion rod in the implant holder. After the insertion rod has been screwed fully into the implant holder, the pin 2 is engaged completely in the conical portion of the recess 12. It then comes into engagement with the inner wall of the recess by clamping the flexible link 4 against this wall. The crushing of the braid, which results from this clamping against the inner wall of the recess, gives some elasticity, albeit very slight, to the engagement of the pin in said recess.

The implant holder 5 can then be unscrewed from the wedge 1, optionally after unscrewing the insertion rod from the implant holder (not obligatory). The pin 2 then detaches automatically from the end of the insertion rod 6 remaining in place in the unthreaded conical portion of the recess 12. For this purpose, the force with which the pin 2 is connected to the end 62 of the insertion rod 2 is calibrated so as to be less than the clamping pressure applied to the pin 2 by the inner wall of the unthreaded conical portion of the recess 12 when the pin is engaged completely therein, and by the force of reaction to the clamping of the one or more flexible links.

During the procedure of inserting the pin 2 into the recess 12, the stabilizing wedge 1 can be held by the surgeon in a position with the cords 4a and 4b of the strap 4 engaged around the spinous processes of the vertebrae to stabilized, thanks in particular to the gripping zone 54 of the implant holder 5.

The implant holder thus simultaneously serves to maintain the stabilizing wedge in position against the vertebrae in the critical step of inserting the blocking pin of the flexible link 4, but also as an instrument for aligning, guiding and inserting the pin through the rod 6 which slides in the internal channel 52 of the implant holder.

Once the implant holder 5 has been separated from the wedge 1 (which is thus already in a situation stabilizing the vertebrae), the locking screw 3 can be engaged in the internally threaded portion 11 of the recess 12 provided in the wedge, as is shown in FIG. 6A and in FIG. 6B. It will be noted that, in this step, the flexible link is already blocked by the pin 2, by clamping of the end portions 41*a* and 42*a* against opposite portions of the inner wall of the recess 12, as shown in FIG. 5A and in FIG. 5B.

The screw 3 and the conical pin 2 allow the clamping pressure exerted on the flexible link 4 to be controlled without recourse to a device for measuring the force or the torque.

For this purpose, the length of the conical pin 2 along its longitudinal direction is calibrated such that its plane contact surface 22 is very slightly above the countersink of the internally threaded hole 11 of the stabilizing wedge 1 when it is inserted according to the technique described above. The plane bearing face 32 of the screw 3 then abuts against the countersink of the internally threaded hole 11, hence abutting against the plane contact surface 22 of the conical pin 2, at the rear end, as is shown in FIG. 7A and in FIG. 7B.

The screw 3 is screwed into the internally threaded hole 11 by hand for example, or with the aid of a screwdriver, for example one with a hexagonal head. When the plane surface 32 of the clamping screw comes into contact with the contact surface 22 of the blocking bolt, the clamping screw drives the blocking pin 2 farther into the recess 12, until the plane surface 32 of the clamping screw meets the countersink of the internally threaded hole 11 which forms a shoulder. The axial advance of the conical pin 2 is then blocked by this shoulder, ensuring that the pressure exerted by the conical pin 2 on the flexible link 4 no longer increases, even if the surgeon continues to exert a torque on the clamping screw 3 with the aid of the screwdriver.

In this position, the screw 3 prevents any movement of the pin 2 that would tend to make it leave the recess 12, for example under the effect of tension exerted on the flexible link 4 by the everyday movements of the patient. This is the locking function of the screw 3.

The originality of the function of the blocking pin according to embodiments of the invention lies in the direction of movement of the pin, which is orthogonal to the direction of the force with which the pin bears against the surface of the strap 4 and against the inner wall of the recess 12 provided in the wedge. The pin indeed moves only along the axis of the posterior approach, which limits the extent of the surgical intervention zone.

The solution described in the present description also makes it possible to install a locking screw 3 which provides safety (locking in position) of the blocking pin 2 of the strap 4, and it permits control of the exerted pressure by virtue of the control of the axial movement of the conical pin 2 in the recess 12. This screw is also put in place and clamped only along the direction of the axis of the posterior approach.

In other words, and following the main advantage of the embodiments described, no action on the part of the surgeon and no movement of a movable component is performed along a lateral direction. Everything is done along the axis of the posterior approach.

The stabilizing wedge 1 can be made of a polymer, for example polyether ether ketone (PEEK). It can be obtained by machining from a bar or block of raw material, by injection molding, 3D printing, or by any other equivalent technique.

The conical blocking pin 2 is preferably made of titanium alloy, chosen for its mechanical strength and its biocompatibility. It can be obtained, for example, by machining from a bar of raw material.

The clamping and blocking locking screw 3 can also be of titanium alloy, for the same reasons and with the same advantages. It can be obtained by machining from a bar of raw material.

The flexible link 4 is preferably manufactured as a braided textile. As has already been mentioned above, the ends of the flexible link can be stiffened so as to facilitate their gripping and their guiding through the passages 13, 14 and 17 provided in the body of the stabilizing wedge 1.

Figure 8:
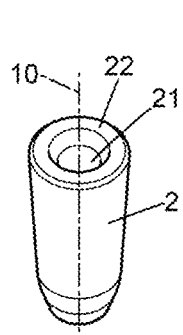
FIG. 8 is a three-dimensional view of an embodiment of the blocking pin.
Figure 9A:
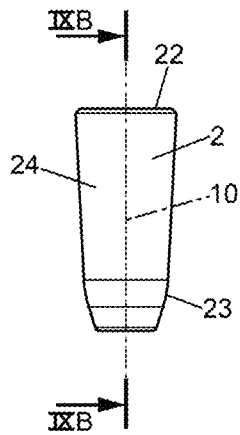
FIGS. 9A, 9B and 9C show a front view, a sectional side view and a plan view, respectively, of the pin from FIG. 8.
Figure 9B:
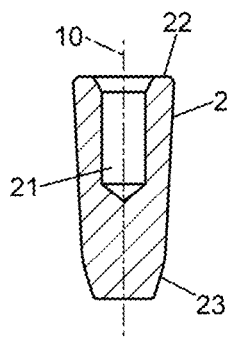
Figure 9C:
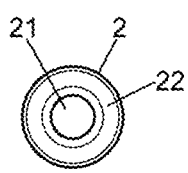

Referring to FIG. 8 and to FIGS. 9A, 9B and 9C, the pin has a frustoconical general shape. At the more tapered end, called the "front" end, that is to say the end via which the pin is inserted into the recess along the axis of the posterior approach, and that is to say also the end that is opposite the "rear" end provided with the aforementioned bearing surface 22, the pin is provided with a rounded end 23. This rounded end facilitates its passage between the strap portions of the strap 4 when they are tensioned in the recess 12 provided in the body 1 of the stabilizing wedge.

In the embodiment shown here, the pin 2 comprises a recess 21 extending along its longitudinal axis 10, for example with a diameter equal to 2 mm, which opens out at the rear end 22 of the pin. This recess is able to receive a connecting piece, which will be discussed later, which has the function of fixing the pin detachably to the end of the insertion rod 6. However, this connection is not obligatory, and the pin can simply be pushed with the aid of the insertion rod 6, after its introduction into the internal channel 52 of the implant holder 5, as far as the recess 12 provided in the body 1 of the wedge 1.

The central shaft of the pin 4 has a larger diameter at the rear end 22, for example 4.4 mm, and a smaller diameter, for example 3.9 mm, at the front end. The dimensions given above are purely illustrative of a non-limiting embodiment given for the requirements of the present description.

As has been stated above, means can be provided for fixing the pin detachably to the insertion rod 6, at the end 62 thereof. This fixing is not obligatory, as has previously been indicated. However, it affords the advantage of avoiding manipulation of the pin alone, which is a small component, above the surgical field. This limits the risk associated with the pin possibly falling, either in the implantation site or beyond. The detachable connection of the pin to the rod also makes it possible to control the advance of the pin 2 along the longitudinal axis of the recess 12, provided in the body of the wedge, by the screwing of the insertion rod, as will be seen hereinafter.

The connection of the pin 2 to the insertion rod 6 can be effected by an intermediate connection piece 7, such as the ferrule shown in FIG. 10.

The ferrule 7 here comprises, on the one hand, a first end part 71 which is threaded. This part 71 is adapted to cooperate with the internal thread of an internally threaded recess which is provided at the second end 62 of the insertion rod 6 and which extends along the longitudinal direction 10 of said rod 6.

The nozzle 7 has, on the other hand, a second end part 72, which can be slightly conical, without being threaded. This part 72 is adapted to be engaged by force in the recess 21 which is provided at the rear of the blocking pin 2 and which has been presented above with reference to FIG. 8 and to FIGS. 8, 9B and 9C. The slightly conical shape of the second part of the ferrule facilitates this procedure of engagement by force.

Figure 11:
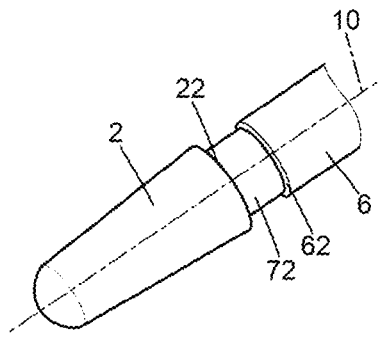
FIG. 11 is a three-dimensional view of the insertion rod with the connecting piece from FIG. 10 partially engaged in a recess at the rear of the blocking pin.

In FIG. 11, the ferrule 7 is shown with the first part 71 fully screwed into the recess provided at the end 62 of the insertion rod 6. Furthermore, the second part 72 of the ferrule is here only partially engaged in the recess 21 provided at the rear 22 of the pin 2.

It is preferable to bring the pin and the rod together until the entire part 72 of the ferrule 7 is engaged in the recess 21 of the pin, that is to say until the end 62 of the rod comes into contact with the rear face 22 of the pin 2. This procedure is performed by the surgeon gripping the pin 2 in one hand and the rod 6 in the other hand. Small movements of rotation between the pin and the rod can be performed simultaneously to the application of a joining force between these two elements, so as to facilitate the total engagement of the pin over the part 72 of the ferrule.

Figure 12:
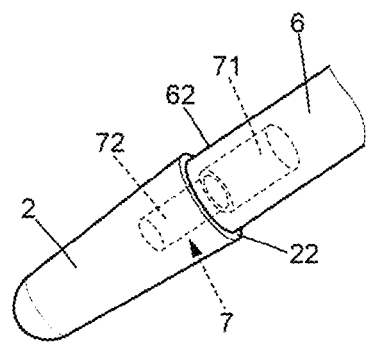
FIG. 12 corresponds to FIG. 11 when the connecting piece is fully engaged in the recess at the rear of the blocking pin; the internal channel of the implant holder fixed to the stabilizing wedge during the placement of the blocking pin.

FIG. 12 shows the pin 2 after full completion of its connection to the end 62 of the insertion rod 6. In this figure, the ferrule 7 is no longer visible, and it has been shown in phantom (i.e. by broken lines) in order to illustrate how the connection of the pin 2 and the rod 6 is effected.

The part 71 performs the detachable fixing of the blocking pin 2 to the insertion rod 6. In fact, once the pin 2 has been put in place in the recess 12 provided in the wedge 1 while a tension was exerted on the one or more flexible links 4, the tensioning force that was exerted on the links 4 is relaxed, and the links then remain wedged against the walls of the recess 12 and thus retain their tensioning. The implant holder 5 is then unscrewed from the stabilizing wedge 1, still with the insertion rod 6 screwed inside the internal channel 51 of the implant holder 5. This exerts a rearward traction on the insertion rod 6 along the longitudinal direction. The part 71 of the ferrule 7 then disengages from the pin 2, while the pin remains in engagement in the recess 12 provided in the body of the wedge.

The ferrule 7 can be made of PE, PET or PEEK, or similar, by machining, molding, 3D printing, or similar. In view of the deformation it may undergo when inserted with force into the rear of the blocking pin 2, the ferrule is preferably disposable. It is for this reason in particular that it is in the form of an independent component that can be screwed onto the end 62 of the rod 6. It can in fact be replaced after each intervention, while the implant holder and the insertion rod are made of stainless steel and can be reused.

Preferably, the kit is made available to the surgeon with the ferrule 7 already screwed into the insertion rod 6. Moreover, the kit can also be supplied with the pin 2 already coupled to the insertion rod via the ferrule 7. However, the surgeon himself may prefer to assemble the pin on the part 72 of the ferrule, in order to be able to assess the strength of the connection thus achieved. The surgeon can thus check that this connection is indeed detachable in the sense that the ferrule will easily disengage from the pin upon withdrawal of the implant holder 5 as described in the preceding paragraph.

The connection between the blocking pin 2 and the insertion rod 6 can also be seen in FIG. 13, which is a sectional view of the insertion rod 2 when introduced into the internal channel of the implant holder 5 for placement of the pin 2 in the recess 11 provided in the body 1 of the stabilizing wedge. In this figure, in which the same elements as in the other figures bear the same reference signs, it will be seen that the implant holder 5 is fixed to the stabilizing wedge 1 and that a flexible link 4 (strap) passes through the recess 12.

In the embodiment shown in FIG. 13, the implant holder is provided with an internal thread 53 at the other of its ends, at a free inlet of the internal channel 52, that is to say the end opposite to the wedge 1 when the implant holder is fixed to said wedge 1. The term "inlet" is used here in reference to the fact that the pin is inserted into the internal channel 52 of the implant holder via this threaded end 53 of the rod. The insertion rod 6 is provided with a complementary thread 61, at its end 62, in order to cooperate with the internal thread 53. In this way, the insertion and then screwing of the insertion rod 6 in the internal channel 52 of the implant holder 5 causes the conical pin 2 to advance into the recess 12 provided in the body 1 of the stabilizing wedge, along the direction of the longitudinal axis 10 of said recess (which then coincides with the longitudinal axis of the internal channel 52). The advance of the pin in this direction is perfectly controlled by controlling the rotation of the insertion rod. This procedure can be performed by the surgeon holding the implant holder 5 in one hand via the gripping part 54 of said implant holder, and rotating the insertion rod 6 with the other hand via the gripping part 64 of said rod.

It will be noted that it is advantageous that the insertion of the pin along the longitudinal axis of the recess 12 is effected by rotation of the pin about said axis. Indeed, the resulting helical movement of the pin facilitates the insertion thereof into the recess and limits the stress on the flexible links that it wedges against the inner wall of the recess. More particularly, the friction of the pin 2 on the surface of the flexible links, or strap surface, is distributed between a component orthogonal to the longitudinal direction of the strap and a component parallel to said longitudinal direction. This also limits the risk of the strap not folding on itself along the direction orthogonal to the longitudinal axis of the strap.

This additional advantageous effect is not obtained if the pin 2 is simply pushed longitudinally by the insertion rod 6, that is to say without screwing thereof in the implant holder (for example if the rod slides in the internal channel 52 of the implant holder without rotating about its longitudinal axis 10). Similarly, this effect is not obtained without the connection between the pin 2 and the insertion rod 6.

When the insertion rod has been screwed completely into the internal channel 52 of the implant holder, the blocking pin is fully inserted in the recess 12 provided in the stabilizing wedge. This result is guaranteed by the design of the various elements of the kit, in particular the axial length of the pin and that of the insertion rod, and the axial length of the internal threads 11 and 53.

The implant holder can then be separated from the stabilizing wedge, by unscrewing it from the internally threaded portion 11 of the recess 12 provided in said wedge, leaving the pin 2 in place in said recess, as has been mentioned above.

Figure 14:
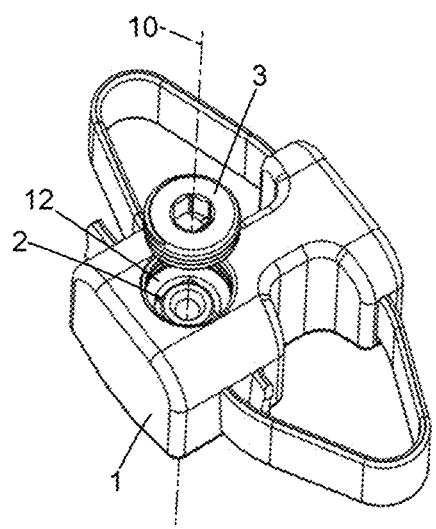
FIG. 14 is a three-dimensional view of the stabilizing wedge, with the blocking pin engaged in the recess, before placement of the locking screw.

FIG. 14 is a three-dimensional view of the stabilizing wedge with the blocking pin 2 engaged in the recess, after separation of the implant holder 5 from the stabilizing wedge 1, and before placement of the locking screw 3. It will be noted again that the blocking of the flexible link 4 is effective with the conical pin 2 alone, the locking screw 3 being merely an additional safety measure.

Advantageously, the same internally threaded part 11 at the inlet of the recess 12 in the stabilizing wedge is used again, this time for the placement of the locking screw 3. In other words, the internal thread 11 serves successively for the temporary fixing of the implant holder 5 on the wedge 1 during the operation, then for the placement of the locking screw 3, which permanently secures the position of the pin 2 in the recess 12. The design of wedge according to the described embodiments is therefore particularly simple. A reduced number of parts and elements allows the blocking pin to be put in place by manual procedures that the surgeon carries out exclusively along the axis of the posterior approach.

The invention has been described and illustrated in the present detailed description and in the figures, in particularly advantageous embodiments. However, it is not limited to the embodiments presented. Other variants and embodiments may be deduced and implemented by a person skilled in the art upon reading the present description and the attached drawings.

In particular, the fixing of the implant holder 5 on the wedge 1 can be effected in a different way from the screwing described above. For example, this fixing can be obtained using a "bayonet" mechanism or any other form of snap-fit connection.

In addition, the connection between the pin 2 and the insertion rod 6 can be achieved by a connecting piece 7 which may differ in its configuration from the ferrule described above with reference to FIG. 10. For example, the part 7 can be an elastic connecting piece. For example, it can be a cylinder or sleeve of a deformable elastic material, for example elastomeric material. This part 7 cooperates with the recess 21 at the rear 22 of the blocking pin 2, and with an unthreaded recess provided at the first end 62 of the insertion rod 6. When a first end part of the sleeve is fitted into the first recess above, and the second end part of the sleeve is fitted into the second recess above, the sleeve provides the detachable fixing of said blocking pin to the insertion rod.

For this purpose, the diameter of the sleeve 7 is slightly greater than the diameter of the recess 21 which is provided in the pin 2. Thus, the sleeve 7 can be introduced by force into the channel 21 via the rear end 22 of the pin 2, playing on its elasticity. A part of the sleeve is left outside the channel 21 and protrudes rearwardly from the end 22 of the pin. The surgeon then fits this free end of the sleeve 7, whose other end remains engaged in the pin 2, inside the recess at the end 62 of the insertion rod. The diameter of this recess is slightly less than the diameter of the part 7. In other words, the rod 6 is thus fitted over the sleeve 7 until the edge of the end 62 of the rod comes into contact with the rear edge 22 of the blocking pin 2. The order of the above two procedures may be reversed.

In the claims, the terms "comprises" or "has" do not exclude other elements or other steps. The various features disclosed and/or claimed may be advantageously combined. Their presence in the description or in various dependent claims does not exclude this possibility. The reference signs must not be understood as limiting the scope of the invention.

The invention claimed is:

1. A surgical kit comprising:
an intervertebral implant with:
a stabilizing wedge configured to stabilize at least two adjacent vertebrae by interposition between spinous processes of the vertebrae, having a substantially parallelepipedal body which has a defined main axis and in which a recess is provided having a defined longitudinal axis parallel to the main axis of the body of the stabilizing wedge, and at least one strap forming a flexible link to fix the stabilizing wedge to the spinous processes of the vertebrae to be stabilized, said strap having first and second portions which each comprise one of the opposite ends of said strap; and
an implant holder having an elongate body along a defined longitudinal axis and with a first end and a second end, and having fixing means which are provided at the first end and which are configured to cooperate with associated means provided at the body of the stabilizing wedge of the implant for fixing the implant holder to the body of the stabilizing wedge in such a way that the elongate body of said implant holder is in parallax with said recess, the recess provided in the body of the stabilizing wedge comprising an inner wall extending parallel to the longitudinal axis of the recess and having a defined shape, at least the first strap portion being configured to pass through the recess perpendicularly with respect to the longitudinal axis of said recess;
wherein the intervertebral implant further comprises a blocking pin having a defined longitudinal axis and a defined shape substantially complementing the shape of the recess provided in the body of the stabilizing wedge, in order to come into engagement with said stabilizing wedge by movement in said recess in the direction of the longitudinal axis of said recess, to immobilize the strap with respect to the stabilizing wedge by clamping the strap portion between the blocking pin and the inner wall of the recess, and
the elongate body of the implant holder is tubular with an internal channel extending along the longitudinal axis of the elongate body of the implant holder and having an internal diameter slightly larger than a largest diameter of the blocking pin of the implant, in order to allow said blocking pin to be inserted and guided through said internal channel, as far as the recess provided in the body of the stabilizing wedge, in the direction of the longitudinal axis of said recess, when the implant holder is fixed to the stabilizing wedge.

2. The surgical kit as claimed in claim 1, wherein:
the recess provided in the body of the stabilizing wedge has an internally threaded inlet zone, and
the tubular body of the implant holder has, at its first end, a thread configured to cooperate with the internal thread of the inlet zone of the recess in order to fix the implant holder to the stabilizing wedge by screwing.

3. The surgical kit as claimed in claim 2, further comprising a screw of the same diameter as the diameter of the inlet zone of the recess provided in the body of the distributing wedge, with a thread configured to cooperate with the internal thread of said inlet zone, and with a bearing zone configured to bear against a contact zone at the rear of the blocking pin in order to axially lock the engagement of the blocking pin in the recess provided in the stabilizing wedge and thus the blocking of the strap.

4. The surgical kit as claimed in claim 2, further comprising:
an insertion rod for the blocking pin, having a first end and a second end and being configured to slide in the internal channel of the tubular body of the implant holder to insert and guide the blocking pin through the internal channel of the implant holder as far as the recess provided in the body of the stabilizing wedge.

5. The surgical kit as claimed in claim 2, wherein the strap has a defined longitudinal direction and a defined strap surface, and the blocking pin is configured to come into engagement with the stabilizing wedge by movement inside the recess provided in the body of the stabilizing wedge, such that the longitudinal axis of the blocking pin:
coincides with the longitudinal axis of the recess,
is perpendicular to the longitudinal axis of the strap portion inside the recess; and
thirdly is parallel to the surface of the first strap portion inside the recess.

6. The surgical kit as claimed in claim 1, further comprising:
an insertion rod for the blocking pin, having a first end and a second end and being configured to slide in the internal channel of the tubular body of the implant holder to insert and guide the blocking pin through the internal channel of the implant holder as far as the recess provided in the body of the stabilizing wedge.

7. The surgical kit as claimed in claim 6, further comprising a connecting piece configured to fix the blocking pin detachably to the second end of the insertion rod.

8. The surgical kit as claimed in claim 7, wherein:
the blocking pin has, at the rear, a recess extending in the longitudinal direction of said pin,
the second end of the insertion rod comprises an internally threaded recess extending in the longitudinal direction of said rod, and
the connecting piece is a ferrule having
a first threaded end part configured to cooperate with the internal thread of the recess provided at the second end of the insertion rod, and
a second, conical end part configured to be engaged by force into the recess provided at the rear of the blocking pin in order to achieve the detachable fixing of said blocking pin to said insertion rod.

9. The surgical kit as claimed in claim 8, wherein the implant holder is provided with an internal thread at its second end, at a free inlet of the internal channel when the implant holder is fixed to the stabilizing wedge, and
the insertion rod is provided, at its first end with a thread in order to cooperate with said internal thread such that the insertion and then the screwing of the insertion rod into the internal channel of the implant holder drives the blocking pin that is a conical pin inside the recess provided in the body of the stabilizing wedge in the direction of the longitudinal axis of said recess.

10. The surgical kit as claimed in claim 8, wherein the strap has a defined longitudinal direction and a defined strap surface, and
the blocking pin is configured to come into engagement with the stabilizing wedge by movement inside the recess provided in the body of the stabilizing wedge, such that the longitudinal axis of the blocking pin:
coincides with the longitudinal axis of the recess,
is perpendicular to the longitudinal axis of the strap portion inside the recess; and
is parallel to the surface of the first strap portion inside the recess.

11. The surgical kit as claimed in claim 7, wherein the implant holder is provided with an internal thread at its second end, at a free inlet of the internal channel when the implant holder is fixed to the stabilizing wedge, and
the insertion rod is provided, at its first end with a thread in order to cooperate with said internal thread such that the insertion and then the screwing of the insertion rod into the internal channel of the implant holder drives the blocking pin that is a conical pin inside the recess provided in the body of the stabilizing wedge in the direction of the longitudinal axis of said recess.

12. The surgical kit as claimed in claim 7, wherein the strap has a defined longitudinal direction and a defined strap surface, and
the blocking pin is configured to come into engagement with the stabilizing wedge by movement inside the recess provided in the body of the stabilizing wedge, such that the longitudinal axis of the blocking pin:
coincides with the longitudinal axis of the recess,
is perpendicular to the longitudinal axis of the strap portion inside the recess; and
is parallel to the surface of the first strap portion inside the recess.

13. The surgical kit as claimed in claim 2, wherein the implant holder is provided with an internal thread at its second end, at a free inlet of the internal channel when the implant holder is fixed to the stabilizing wedge, and
the insertion rod is provided, at its first end with a thread in order to cooperate with said internal thread such that the insertion and then the screwing of the insertion rod into the internal channel of the implant holder drives the blocking pin that is a conical pin inside the recess provided in the body of the stabilizing wedge in the direction of the longitudinal axis of said recess.

14. The surgical kit as claimed in claim 13, wherein the strap has a defined longitudinal direction and a defined strap surface, and
the blocking pin is configured to come into engagement with the stabilizing wedge by movement inside the recess provided in the body of the stabilizing wedge, such that the longitudinal axis of the blocking pin:
coincides with the longitudinal axis of the recess,
is perpendicular to the longitudinal axis of the strap portion inside the recess; and
is parallel to the surface of the first strap portion inside the recess.

15. The surgical kit as claimed in claim 6, wherein the strap has a defined longitudinal direction and a defined strap surface, and
the blocking pin is configured to come into engagement with the stabilizing wedge by movement inside the recess provided in the body of the stabilizing wedge, such that the longitudinal axis of the blocking pin:
coincides with the longitudinal axis of the recess,
is perpendicular to the longitudinal axis of the strap portion inside the recess; and
is parallel to the surface of the first strap portion inside the recess.

16. The surgical kit as claimed in claim 1, wherein the strap has a defined longitudinal direction and a defined strap surface, and
the blocking pin is configured to come into engagement with the stabilizing wedge by movement inside the recess provided in the body of the stabilizing wedge, such that the longitudinal axis of the blocking pin:
coincides with the longitudinal axis of the recess,
is perpendicular to the longitudinal axis of the strap portion inside the recess; and
thirdly is parallel to the surface of the first strap portion inside the recess.

17. The surgical kit as claimed in claim 1, wherein:
the strap has a defined longitudinal direction and a defined strap surface,
each of the first and second strap portions is configured to pass through the recess provided in the stabilizing wedge, in order for the strap to form at least one loop in a plane perpendicular to the main axis of the wedge, with at least one cord configured to come into engagement with one of the spinous processes of two vertebrae to be stabilized, and the blocking pin is configured to come into engagement with the stabilizing wedge in the direction of the main axis of the body of said wedge, between each of the first and second strap portions inside the recess, such that the longitudinal axis of the pin:

coincides with the longitudinal axis of the recess, is perpendicular to the longitudinal axis of each of the two portions of the strap inside the recess, and thirdly is parallel to the surface of each of the first and second strap portions inside the recess, and such that each of the first and second strap portions is immobilized with respect to the stabilizing wedge by said strap portions being clamped between the blocking pin and respective portions of the inner wall of the recess that face each other.

18. The surgical kit as claimed in claim 17, wherein the first and second strap portions are configured to pass in opposite directions through the recess provided in the body of the stabilizing wedge, to intersect in said recess, and in order for the strap to form a loop in a plane perpendicular to the main axis of the wedge, with two cords which are located respectively on either side of the stabilizing wedge in said plane and are configured to come into engagement each with a respective one of the spinous processes of two adjacent vertebrae to be stabilized.

* * * * *